United States Patent
Burkhart et al.

(10) Patent No.: US 11,478,239 B2
(45) Date of Patent: *Oct. 25, 2022

(54) POINT-LOADING KNOTLESS FIXATION DEVICES

(71) Applicant: Arthrex, Inc., Naples, FL (US)

(72) Inventors: Stephen S. Burkhart, Boerne, TX (US); Thomas Dooney, Jr., Naples, FL (US); Derek C. Sullivan, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/705,870

(22) Filed: Mar. 28, 2022

(65) Prior Publication Data

US 2022/0211364 A1 Jul. 7, 2022

Related U.S. Application Data

(63) Continuation of application No. 16/527,866, filed on Jul. 31, 2019, now Pat. No. 11,284,876, which is a continuation of application No. 14/989,451, filed on Jan. 6, 2016, now Pat. No. 10,398,426.

(51) Int. Cl.
*A61B 17/04* (2006.01)
*A61F 2/08* (2006.01)
*A61B 17/06* (2006.01)

(52) U.S. Cl.
CPC ...... *A61B 17/0401* (2013.01); *A61B 17/0485* (2013.01); *A61F 2/0811* (2013.01); *A61B 2017/0403* (2013.01); *A61B 2017/044* (2013.01); *A61B 2017/0409* (2013.01); *A61B 2017/0412* (2013.01); *A61B 2017/0458* (2013.01); *A61B 2017/0464* (2013.01); *A61B 2017/0496* (2013.01); *A61B 2017/06185* (2013.01); *A61F 2002/0841* (2013.01); *A61F 2002/0852* (2013.01); *A61F 2002/0888* (2013.01); *A61F 2250/0007* (2013.01); *A61F 2250/0012* (2013.01)

(58) Field of Classification Search
CPC . A61B 17/04; A61B 17/0401; A61B 17/0485; A61B 17/06; A61B 17/0403; A61B 17/044; A61B 17/0409; A61F 2/08; A61F 2/0811
See application file for complete search history.

(56) References Cited

U.S. PATENT DOCUMENTS

| | | | |
|---|---|---|---|
| 6,716,234 B2 | 4/2004 | Grafton et al. |
| 7,329,272 B2 | 2/2008 | Burkhart et al. |
| 7,981,140 B2 | 7/2011 | Burkhart |
| 8,439,976 B2 | 5/2013 | Albertorio et al. |
| 8,460,379 B2 | 6/2013 | Albertorio et al. |
| 8,821,541 B2 | 9/2014 | Dreyfuss |
| 8,858,596 B2 | 10/2014 | Robison |
| 9,005,246 B2 | 4/2015 | Burkhart et al. |

(Continued)

*Primary Examiner* — Christopher J Beccia
(74) *Attorney, Agent, or Firm* — Blank Rome LLP

(57) ABSTRACT

Surgical constructs and methods for soft tissue to bone repairs, without knot tying. The soft tissue repair constructs include a fixation device, a flexible strand, and a shuttle/pull device attached to the flexible strand and provided within the body of the fixation device. A splice is formed by pulling on the shuttle/pull device to allow desired tensioning of soft tissue to be fixated or repaired relative to the bone.

20 Claims, 19 Drawing Sheets

(56) References Cited

U.S. PATENT DOCUMENTS

| | | |
|---|---|---|
| 9,107,653 B2 | 8/2015 | Sullivan |
| 9,510,816 B2 * | 12/2016 | McDevitt ............ A61B 17/0401 |
| 10,398,426 B2 | 9/2019 | Burkhart |
| 11,284,876 B2 * | 3/2022 | Burkhart ............ A61B 17/0401 |
| 2007/0156148 A1 * | 7/2007 | Fanton ............... A61B 17/0401 |
| | | 606/326 |
| 2008/0255613 A1 * | 10/2008 | Kaiser ............... A61B 17/06166 |
| | | 606/232 |
| 2013/0023929 A1 | 1/2013 | Sullivan et al. |
| 2013/0165972 A1 | 6/2013 | Sullivan |

* cited by examiner

POINT-LOADING KNOTLESS FIXATION DEVICES

This is a continuation of application Ser. No. 16/527,866, filed Jul. 31, 2019, now U.S. Pat. No. 11,284,876, which is a continuation of application Ser. No. 14/989,451, filed Jan. 6, 2016, now U.S. Pat. No. 10,398,426, the entire disclosures of which are herein incorporated by reference.

BACKGROUND

The present invention relates to surgical devices and methods of tissue repair and, in particular, to devices and methods for repair or fixation of soft tissue to bone without the need for knots.

SUMMARY

The present invention provides knotless tensionable surgical constructs with various designs and methods of fixation of soft tissue to bone with the ability to tension/retension after their implantation. The surgical constructs are provided with flexible constructs comprising a tensionable loop that can be point-loaded by a flexible strand or loop. The tensionable knotless surgical constructs have applicability to soft tissue repairs including labral, rotator cuff, Achilles tendon, and biceps, among others. Methods of tissue repair techniques are also disclosed.

These and other features and advantages of the invention will be more apparent from the following detailed description that is provided in connection with the accompanying drawings and illustrated exemplary embodiments of the invention.

DETAILED DESCRIPTION

Figure 1:
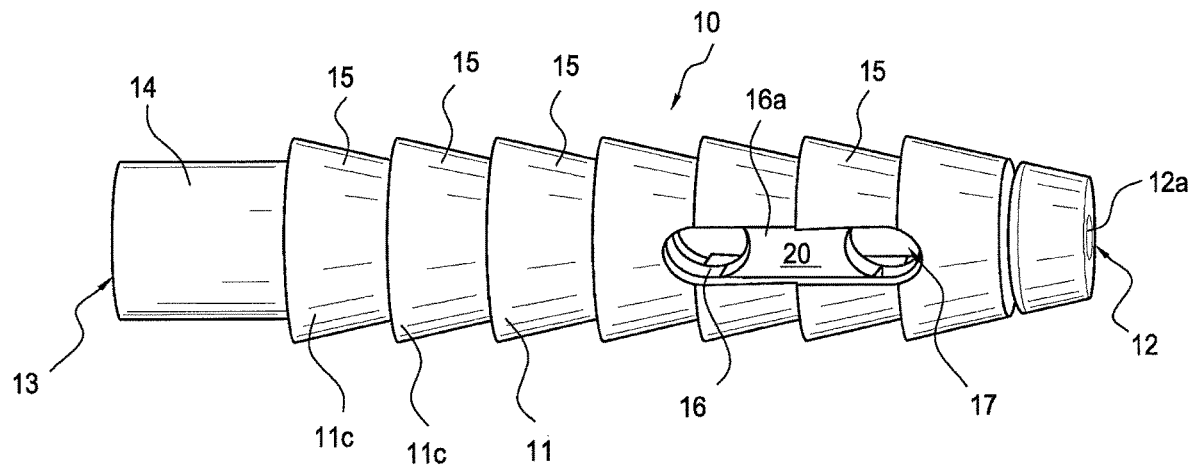
FIG. 1 illustrates a tensionable knotless anchor according to the prior art.

The present invention provides surgical constructs, systems and techniques for knotless soft tissue repair and fixation, such as fixation of soft tissue (ligament, tendon, graft, etc.) to bone. The surgical constructs comprise fixation devices (tensionable knotless anchors) that are inserted into bone with a suture mechanism (flexible construct) formed of a flexible strand (a suture) provided within the fixation device and a shuttle/pull device (a suture passing instrument) attached to the flexible strand. The flexible strand and the shuttle/pull device attached to it allow the formation of a splice within or outside the body of the anchor and during the tissue repair procedure (to finalize the construct). The shuttle/pull device is provided within the strand (inside of the strand) and forms the splice subsequent to the insertion of the fixation device within the bone to allow formation of the final fixation device with a knotless self-locking mechanism that allows the user (for example, the surgeon) to control the tension of the strand on the soft tissue to be attached to bone. The splice may alternatively be formed prior to insertion of the fixation device within bone. The splice creates a tensionable loop that can be point-loaded by additional fixed loops or suture chains that may also be included in the surgical constructs.

At least one of the flexible strand and the shuttle/pull device may be made of any known suture material, such as ultrahigh molecular weight poly ethylene (UHMWPE) or the FiberWire® suture (disclosed in U.S. Pat. No. 6,716,234, the disclosure of which is hereby incorporated by reference in its entirety herewith). Typically the suture will be UHWMPE suture. The shuttle/pull device may be a shuttle/pull suture device such as a FiberLink™ or a Nitinol loop.

The present invention also provides methods of soft tissue repair which do not require tying of knots and allow adjustment of both the tension of the suture and the location of the tissue with respect to the bone. An exemplary method of the present invention comprises inter alia the steps of: (i) providing a surgical construct comprising a fixation device (for example, an anchor) with a flexible strand (for example, suture) and with a first shuttle/pull device (a suture passing instrument) attached to the flexible strand; (ii) installing the fixation device into bone; (iii) passing a suture retrieval instrument through a soft tissue and retrieving a loop of a second shuttling device, the second shuttling device having a tensioning end passing through a second cannula; (iv) pulling the loop of the second shuttling device through the first cannula and passing the flexible strand through the loop of the second shuttling device; (v) pulling the tensioning end of the second shuttling device to pull the flexible strand through a top side of the soft tissue, and passing the flexible strand through a loop of the first shuttling device; and (vi) pulling a tensioning end of the first shuttling device to pull the flexible strand through a splice region of the flexible strand, thereby forming a knotless closed loop having an adjustable perimeter.

The flexible strand may be passed through at least a portion of the body of the fixation device (for example, through a full cannulation of the fixation device, or through a transversal opening at a distal end of the fixation device). Alternatively, the flexible strand may be fixed to the fixation device (which may be solid or cannulated) by overmolding the suture to the anchor body or by compressing the suture against the bone (achieving an interference fit between the fixation device and the bone tunnel, compressing the flexible strand). The splice may be formed within the body of the fixation device or outside the body of the fixation device. Upon insertion into the bone and tensioning, the splice may reside within the body of the fixation device or outside the body of the fixation device (but within a bone tunnel). After tensioning the knotless closed loop to an appropriate tension, a remaining portion of the flexible strand extending out from the splice region may be removed.

Another exemplary method of the present invention comprises inter alia the steps of: (i) providing a surgical construct comprising a fixation device (for example, an anchor), a flexible strand (for example, suture) extending through the body of the fixation device, a shuttle/pull device (a suture passing instrument) attached to the flexible strand, and a fixed loop construct; (ii) installing the fixation device into bone; (iii) passing the fixed loop around or through tissue to be fixated (or reattached) to bone; (iv) passing the flexible strand through the fixed loop, and then capturing a proximal end of the flexible strand with a loop of the shuttling device; (v) pulling a tensioning end of the shuttling device to pull the proximal end of the flexible strand through the splice region in the flexible strand to form an adjustable knotless closed loop; and (vi) tensioning the proximal end of the flexible strand to reduce the perimeter of the knotless closed loop to a desired location and with a desired tension, wherein the knotless closed loop is point-loaded by the fixed loop.

Figure 2:
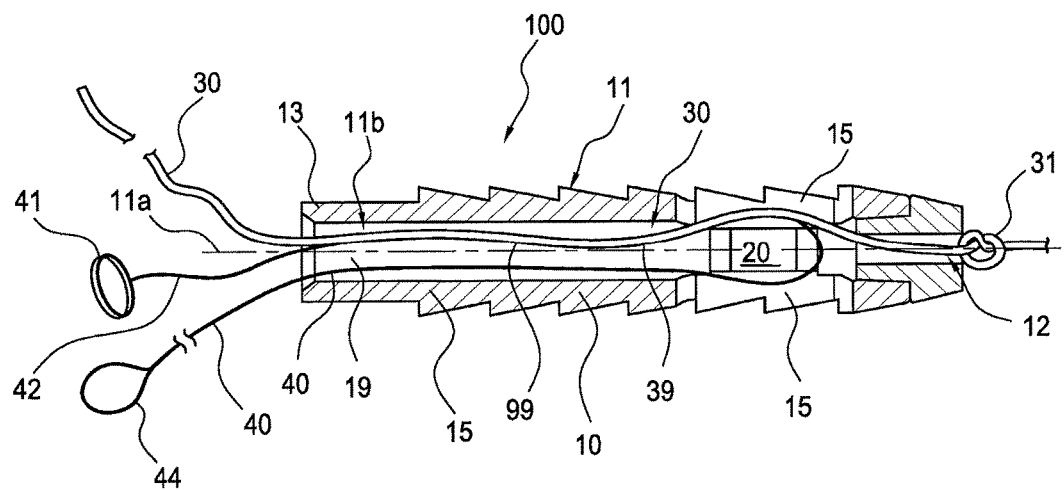
FIG. 2 is a cross-sectional view of a surgical construct according to the prior art (with the tensionable knotless anchor of FIG. 1, a suture and a suture passing device attached to the suture, before tensioning of the suture).

Referring now to the drawings, where like elements are designated by like reference numerals, FIGS. 1 and 2 illustrate a fixation device 10 known in the art.

In the particular embodiment illustrated in FIG. 1, fixation device 10 is a tensionable knotless anchor having an anchor body 11 provided with a longitudinal axis 11*a*, a proximal end 13 and a distal end 12, and a plurality of ribs 15 extending circumferentially around it. Openings/channels 16 and 17 allow threading suture(s) and/or suture passing device(s) to pass around post 20, as detailed below. Cannulation 11*b* extends along the body 11 to allow passage of flexible strands and of suture passing devices.

Cylindrical portion 14 is provided at the proximal end 13 of the anchor 10 and contains a socket 19 (FIG. 2) configured to securely engage a tip of a driver.

Openings/channels 16, 17 are positioned opposite to each other relative to the post 20 and also symmetrically located relative to the post 20, to allow flexible strand 30 (suture 30) and shuttle/pull device 40 (suture passing instrument 40) to pass and slide therethrough. Openings/channels 16, 17 extend in a direction about perpendicular to the longitudinal axis 11*a*, and communicate through recesses 16 *a*, 17*a* with the outer surfaces 11*c* of anchor body 11. Only recess 16*a* is shown in FIG. 1 (recess 17*a* is located on the opposite side of the recess 16*a*, i.e., on the anchor side facing away from the page). The position and size of the openings/channels 16, 17 and recesses 16*a*, 17*a* may be determined according to the characteristics of the flexible strand 30 and shuttle/pull device 40, and of the arthroscopic procedure, and the need to precisely orientate the anchor during insertion to optimize suture sliding characteristics.

FIG. 2 illustrates anchor 10 of FIG. 1 assembled with flexible construct 99 formed of flexible strand or flexible material 30 (suture 30 or tie down suture 30) and shuttle/pull device 40 (suture passing instrument such as FiberLink™ 40 or a nitinol loop 40) attached to the flexible strand 30. Surgical construct 100 (FIG. 2) comprises tensionable knotless anchor 10 provided with flexible strand 30 passing through the body of the tensionable knotless anchor 10 and with shuttle/pull device 40 attached to the flexible strand 30. Flexible strand 30 is secured to anchor 10 by passing through distal blind hole 12*a* and tying a static knot 31.

Figure 3A:
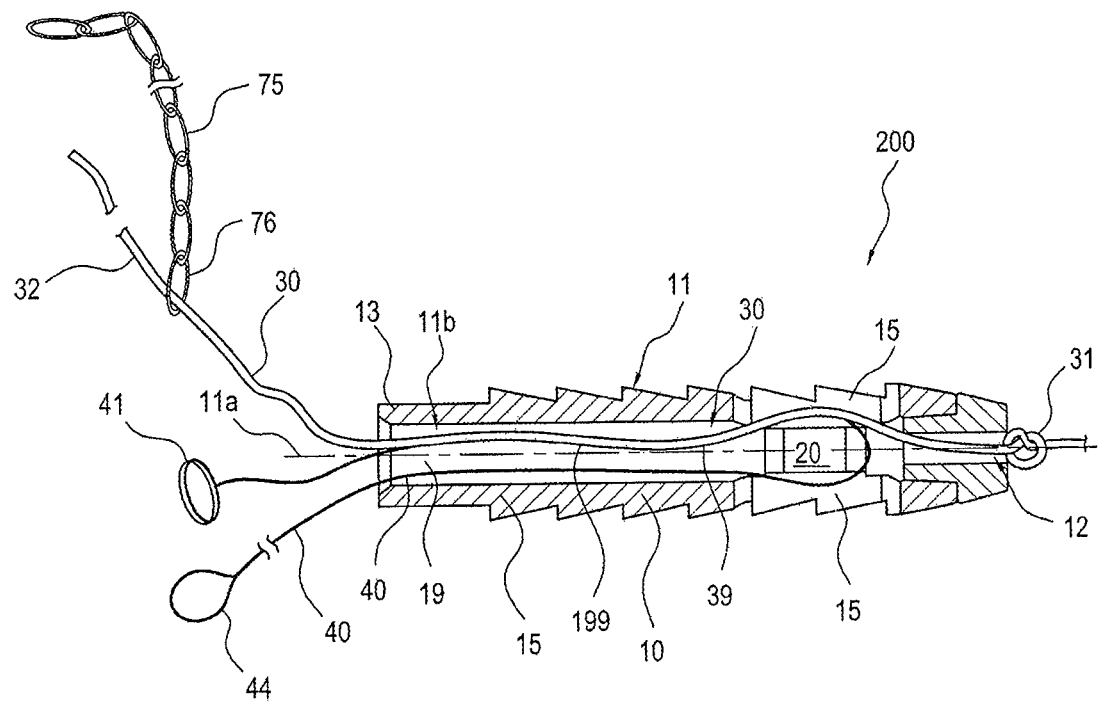
FIGS. 3a and 3b illustrate an exemplary embodiment of a surgical construct according to the present invention.
Figure 3B:
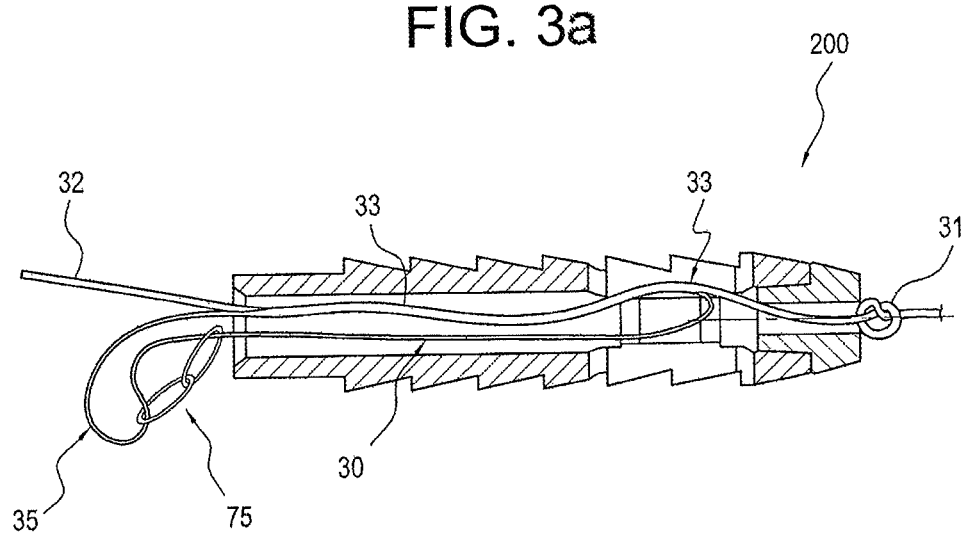

FIGS. 3*a* and 3*b* illustrate an exemplary embodiment of surgical construct 200 according to the present invention. Surgical construct 200 comprises any suitable knotless anchor known in the art, for example tensionable knotless anchor 10 as described above. Tensionable knotless anchor 10 can be provided with flexible construct 199 passing through the body of tensionable knotless anchor 10. Flexible construct 199 comprises flexible strand 30, shuttle/pull device 40 attached to flexible strand 30, and two or more connected flexible loops in the form of a suture chain 75 (for example, Arthrex FiberChain®). Flexible strand end 32 passes through a loop at the end of suture chain 75 (terminating loop 76).

FIG. 3*b* illustrates surgical construct 200 after a tensionable loop 35 is formed by pulling flexible strand 30 through itself using shuttle/pull device 40. As explained in more detail below in conjunction with FIGS. 12-15, flexible strand end 32 is passed through a terminating loop 76 of suture chain 75. Suture chain 75 is passed through a target tissue, and flexible strand end 32 is passed through a second loop of suture chain 75. The second loop can be any other loop in suture chain 75, and does not necessarily have to be the loop adjacent to terminating loop 76. After flexible strand end 32 is passed through a second loop of suture chain 75, the remaining portion of suture chain 75 (the portion not connecting terminating loop 76 to the other loop that flexible strand end 32 is passed through) may be removed and discarded. Flexible strand end 32 is then passed through a loop end 44 of shuttle/pull device 40 (nitinol loop 44), and shuttle/pull device 40 is pulled to pull flexible strand 30 through itself to create splice 33 and tensionable loop 35. As illustrated in FIG. 3*b*, tensionable loop 35 is point-loaded by suture chain 75.

Figure 4:
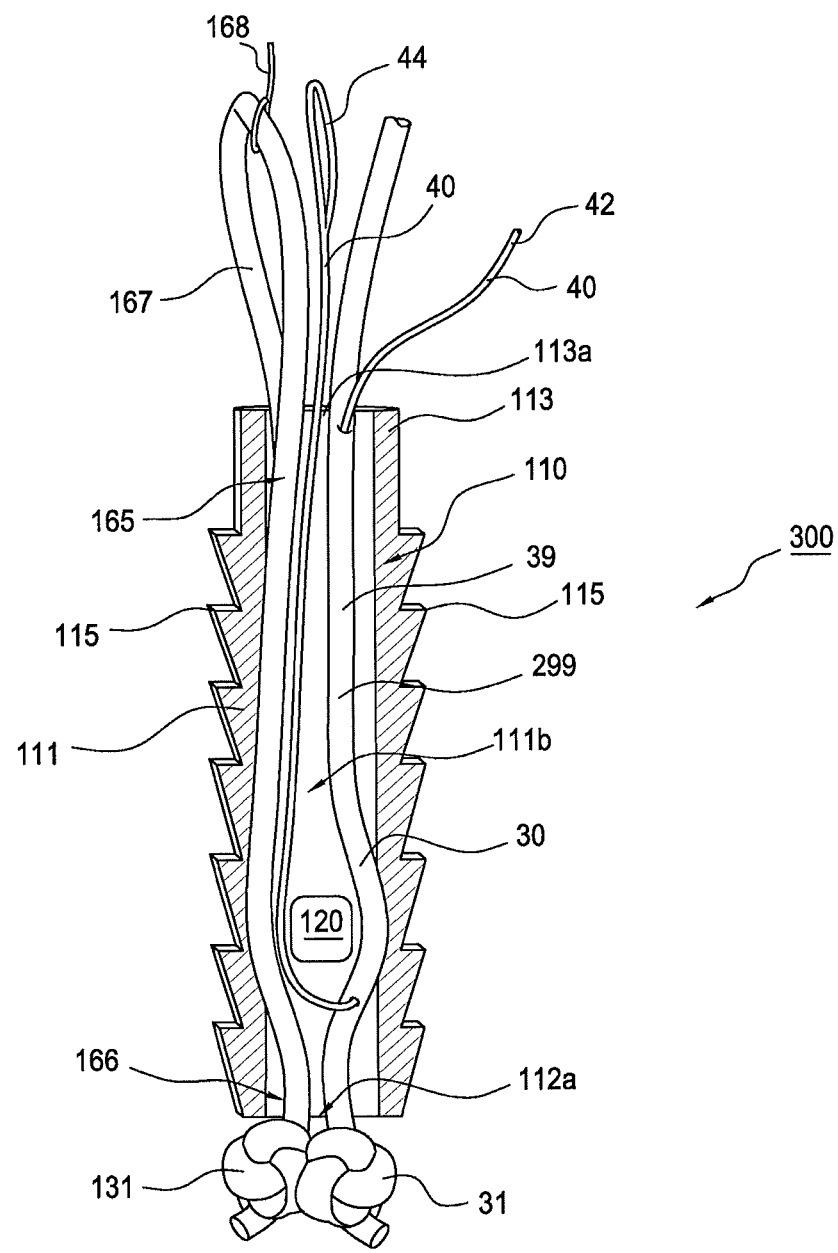
FIG. 4 illustrates another exemplary embodiment of a surgical construct according to the present invention.
Figure 5:
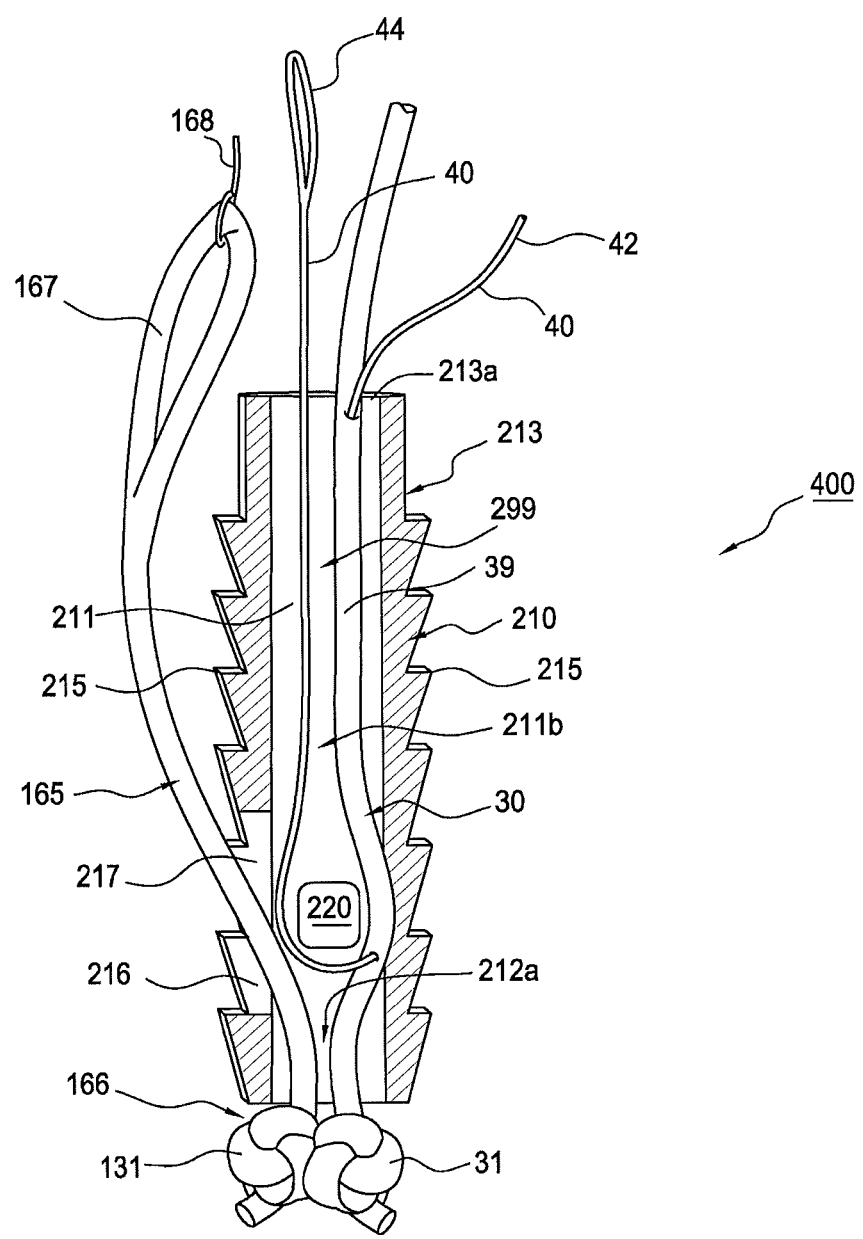
FIG. 5 illustrates another exemplary embodiment of a surgical construct according to the present invention.

FIGS. 4 and 5 illustrate surgical constructs 300, 400 of the present invention. Surgical construct 300 comprises tensionable knotless anchor 110, flexible construct 299, and fixed loop construct 165. Tensionable knotless anchor 110 is about similar to anchor 10 described above with reference to FIGS. 1 and 2, but differs in that it may be used with both flexible construct 299 and an additional fixed loop construct 165 that is affixed to tensionable knotless anchor 110. Fixed loop construct 165 has a distal end 166 and a proximal end comprising a fixed loop 167. Fixed loop construct 165 can be preloaded onto anchor 110 by tying static knot 131, which prevents fixed loop construct 165 from passing through distal blind hole 112*a*. The fixed loop construct 165 may also be preloaded by insert molding or by any other means known in the art. As shown in the embodiment illustrated in FIG. 4, fixed loop construct 165 can pass through cannulation 111*b* and proximal blind hole 113*a*. Cannulation 111*b* must be large enough to accommodate fixed loop construct 165 and flexible construct 299 (comprising flexible strand 30 and shuttle/pull device 40 attached to flexible strand 30).

Similarly, distal blind hole 112a must be large enough for distal end 166 of the fixed loop construct 165 and flexible strand 30 to both pass through. Passing suture 168 may be provided to wrap around fixed loop 167 to aid in passing fixed loop 167 through a target tissue. Passing suture 168 can be any suitable passing suture known in the art, for example Arthrex Fiber Link®.

FIG. 5 illustrates surgical construct 400 comprising knotless anchor 210, flexible construct 299, and fixed loop construct 165. Tensionable knotless anchor 210 is about similar to anchor 110, except that fixed loop construct 165 does not pass through cannulation 211b, and instead extends exteriorly to anchor body 211. Thus, cannulation 211b does not need to be large enough to accommodate both fixed loop construct 165 and flexible construct 299. Fixed loop construct 165 exits anchor 210 at opening 216 or opening 217, located near the distal end of anchor 210. Distal end 166 of fixed loop construct 165 passes through distal blind hole 212a and is secured to anchor 210 by tying a static knot 231. Passing suture 168 may wrap around fixed loop 167 to aid in passing fixed loop 167 through a target tissue.

Figure 6A:
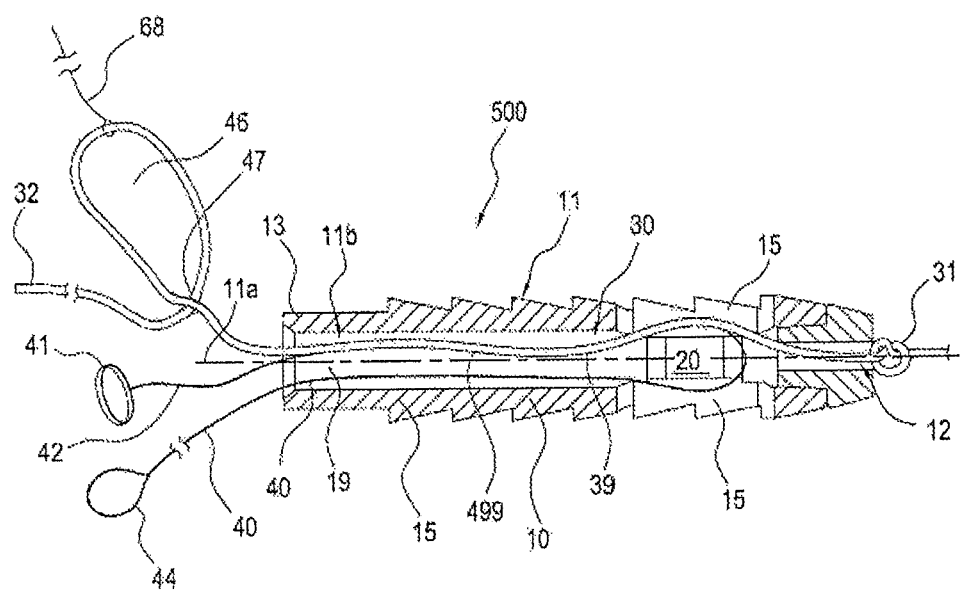
FIGS. 6a and 6b illustrate another exemplary embodiment of a surgical construct according to the present invention.
Figure 6B:
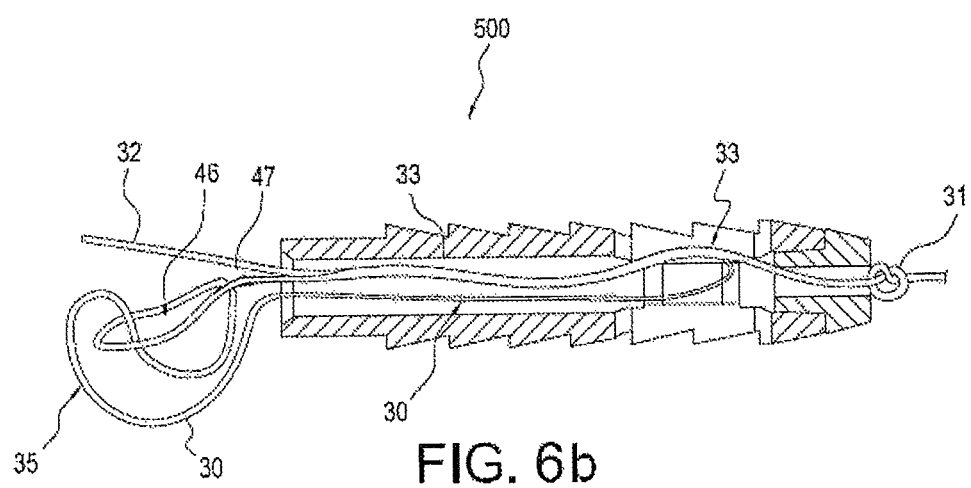

FIGS. 6a and 6b illustrate an exemplary embodiment of surgical construct 500 according to the present invention. Surgical construct 500 comprises any suitable tensionable knotless anchor known in the art, for example tensionable knotless anchor 10. Knotless anchor 10 can be provided with flexible construct 499 passing through the body of tensionable knotless anchor 10. Flexible construct 499 comprises flexible strand 30 and shuttle/pull device 40 attached to flexible strand 30, wherein flexible strand end 32 is threaded through intersection point 47 in flexible strand 30 to create slip-loop 46. Slip-loop 46 may be provided with a passing suture 68 to aid in passing loop 46 through a target tissue.

FIG. 6b illustrates surgical construct 500 after a tensionable loop 35 is formed by pulling flexible strand 30 through itself using shuttle/pull device 40. As explained in more detail below in conjunction with FIGS. 21-24, flexible strand end 32 is passed through an eyelet of a needle, and the needle is passed through flexible strand 30 at an intersection point 47 to create an adjustable slip-loop 46. Flexible strand end 32 is then removed from the eyelet of the needle, and slip-loop 46 is passed through a target tissue. Flexible strand end 32 of flexible strand 30 is then passed through slip-loop 46, and then through a loop end 44 of shuttle/pull device 40 (nitinol loop 44). Shuttle/pull device 40 is then pulled to pull flexible strand 30 through itself to create splice 33 and tensionable loop 35. As illustrated in FIG. 6b, tensionable loop 35 is point-loaded by slip-loop 46, both of which are formed by flexible strand 30, such that tensionable loop 35 may be looped with and through slip-loop 46.

Figure 7:
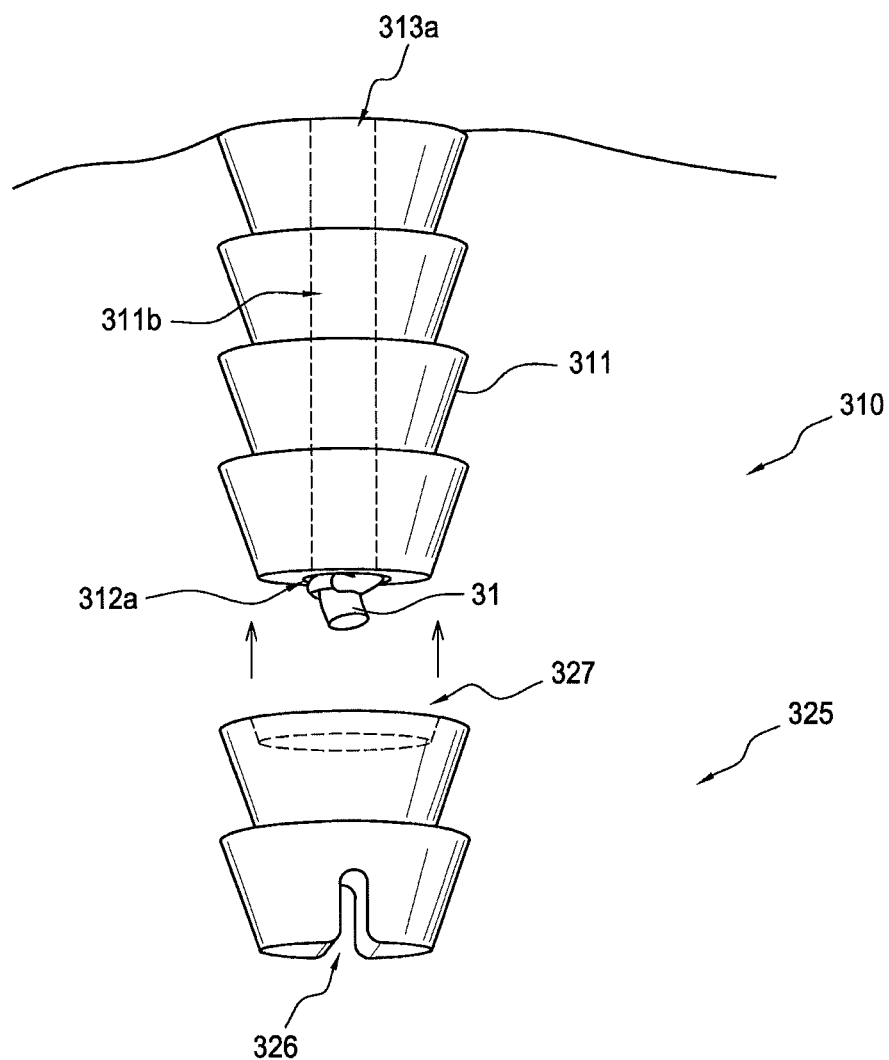
FIG. 7 illustrates an exemplary embodiment of a tensionable knotless anchor according to the present invention.

FIG. 7 illustrates another tensionable knotless anchor 310 of the present invention. Tensionable knotless anchor 310 is about similar to knotless anchors 10, 110, and 210 described above, but differs in that the most distal end of tensionable knotless anchor 310 is provided with an anchor cap 325 having slot 326 at the tip of anchor cap 325. Anchor cap 325 has a hollow section 327 to fit, for example, over the last rib of anchor 310. Anchor cap 325 can be configured to be snapped onto anchor 310, glued to anchor 310, or affixed to anchor 310 using any means known in the art. Anchor 310 can be used with any of the flexible constructs described above.

Flexible strand 30 can be preloaded onto anchor 10, 110, 210, or 310 by tying static knot 31, which prevents flexible strand 30 from passing through distal blind hole 12a, 112a, 212a, or 312a. The flexible strand may also be preloaded by insert molding or by any other means known in the art.

Flexible strand 30 may pass around post 20, 120, 220, which is large enough to allow flexible strand 30 to take gradual turns instead of sharp turns. Flexible strand 30 then passes through cannulation 11b, 111b, 211b, 311b and proximal blind hole 13a, 113a, 213a, 313a. Tensionable knotless anchor 10, 110, 210, 310 is loaded onto a driver (not shown in FIGS. 1-7), and flexible strand 30 is tied to the driver (for example, wrapped around a cleft of the driver) to fasten tensionable knotless anchor 10, 110, 210, 310 securely to the driver. In other exemplary embodiments, anchors 10, 110, 210, and 310 may be configured without post 20, 120, 220.

Figure 8:
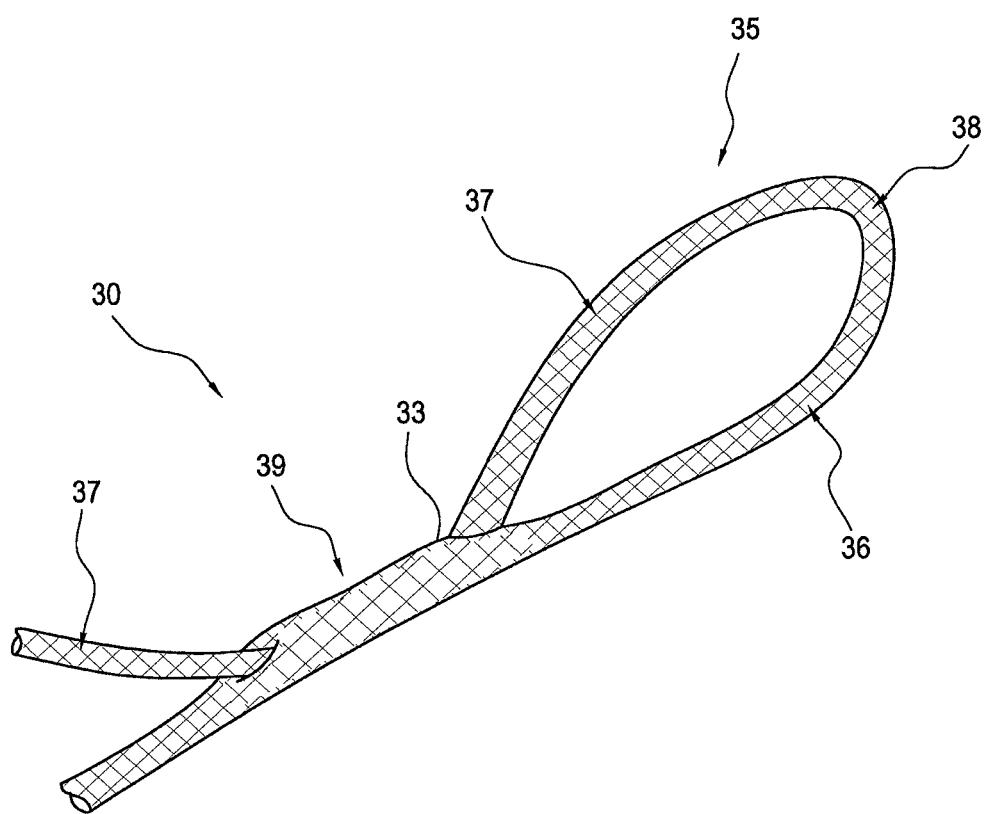
FIG. 8 illustrates a tensionable loop formed of a flexible strand spliced through itself, according to an exemplary embodiment of the present invention.

FIG. 8 illustrates an example embodiment of flexible strand 30 after forming a tensionable loop 35. Flexible strand 30 can have a braided or multi-filament sheath portion 36 and a core portion 37. Core portion 37 is spliced through sheath portion 36 (either pre-formed or by using shuttle/loop device 40) forming splice 33 and splice region 39. Tensionable loop 35 can be comprised of one-half core portion 37 and one-half sheath portion 36, the two portions meeting at or near apex 38 of tensionable loop 35. Tensioning core portion 37 unlocks the core from the sheath and enlarges the diameter of tensionable loop 35. Tensioning sheath portion 36 locks the core and fixes the diameter of tensionable loop 35. Tensioning at apex 38 of tensionable loop 35 keeps the core and the diameter fixed. Thus, point-loading (applying a load or force) tensionable loop 35 at or near apex 38 keeps core portion 37 locked, allowing surgeons to make tensionable loops that will not slip when the loops are point-loaded at or near the apex of the loop.

Prior to the fastening of the anchor 10, 110, 210, 310 to the driver, suture passing device 40 (for example, a FiberLink® or a nitinol loop) is threaded through flexible strand 30 (i.e., attached to the flexible strand 30 through splice region 39). Suture passing device 40 includes an eyelet/loop 44 for passing suture and, optionally, a pull-ring 41 located at tensioning end 42. Suture passing device 40 passes through an aperture of flexible strand 30, located either proximal or distal to distal blind hole 12a, 112a, 212a, or 312a. It then exits an aperture of flexible strand 30, within the tensionable knotless anchor 10, 110, 210, 310, traverses around post 20, 120, 220, and through proximal blind hole 13a, 113a, 213a, 313a. Tensionable knotless anchor 10, 110, 210, 310 loaded with flexible construct 99, 199, 299 (formed at least of flexible strand 30 attached to the suture passing device 40) is then secured into bone (for example, into a hole/socket/tunnel formed in the bone) by using the driver.

Fixed loop construct 165 can be formed of any suitable material known in the art, such as ultrahigh molecular weight poly ethylene (UHMWPE) or the FiberWire® suture (disclosed in U.S. Pat. No. 6,716,234 the entire disclosure of which is hereby incorporated by reference in its entirety herewith). Typically, the fixed loop construct will be UHWMPE suture.

Suture chain 75 can be any suitable suture chain known in the art, for example Arthrex FiberChain®. However, any suture chain consisting of a plurality of consecutive loops may be used.

Surgical constructs 200, 300, 400, and 500 of the present invention offer at least the following advantages:
- the tension and/or location of the tissue may be altered after the tensionable knotless anchor is implanted;
- no knots need to be tied in the suture during the repair or fixation procedure, which makes the procedure faster, easier, and less costly;
- there is no need to load the suture outside of the tensionable knotless anchor;

the suture may be loaded or pre-loaded on the inside of the tensionable knotless anchor; and no additional fasteners need to be used.

Figure 9:
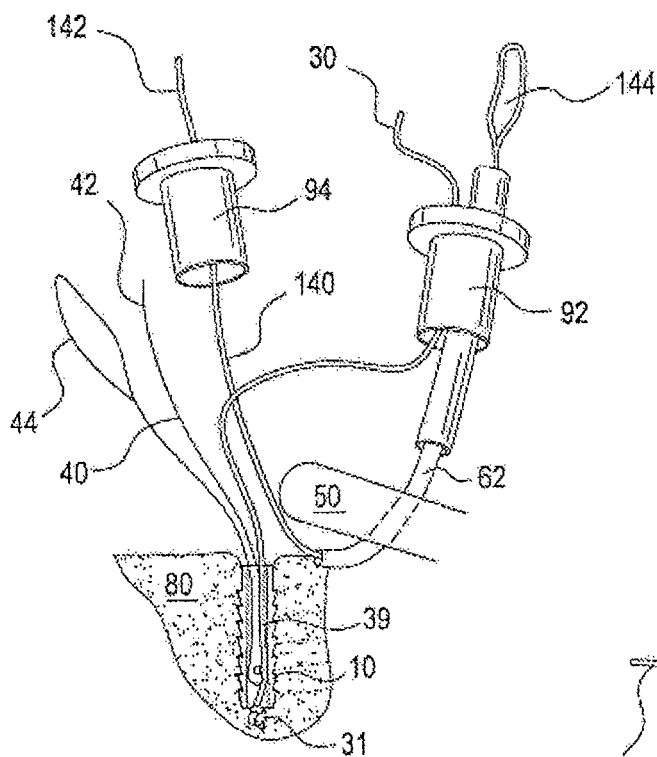
FIGS. 9-11 illustrate subsequent steps of a method of knotless repair according to an exemplary embodiment of the present invention.
Figure 10:
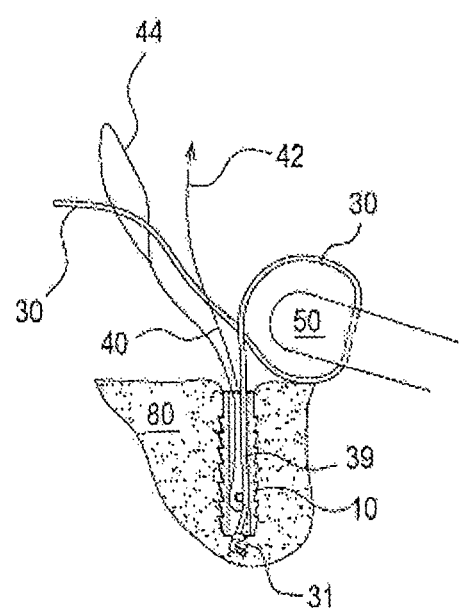
Figure 11:
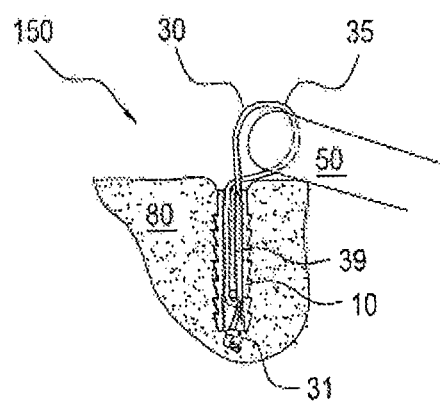
Figure 12:
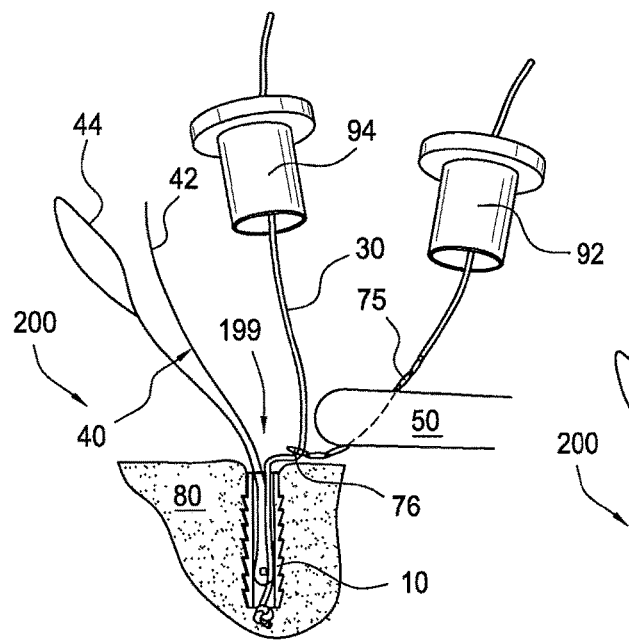
FIGS. 12-15 illustrate subsequent steps of a method of knotless repair according to an exemplary embodiment of the present invention.
Figure 13:
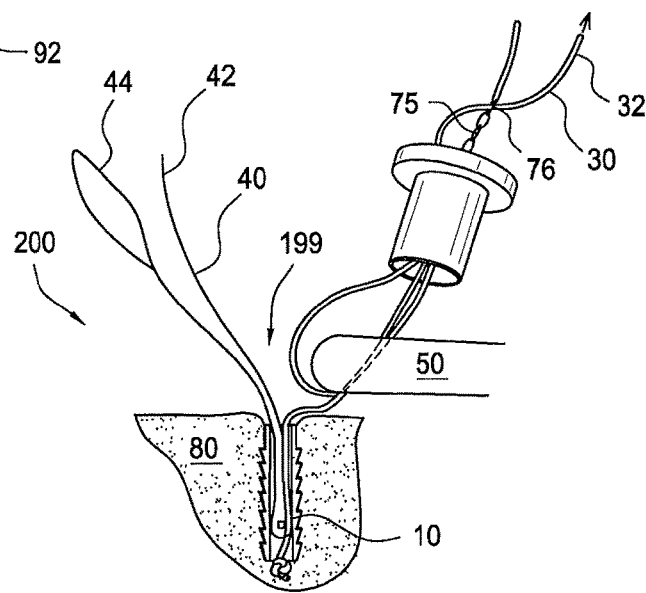

FIGS. 9-11 illustrate surgical construct 100 of FIGS. 1-2 (with knotless tensionable anchor 10, flexible strand 30 and suture passing device 40 attached to the flexible strand 30) employed in an exemplary method of tissue repair 150 (FIG. 11) of the present invention, wherein the knotless suture anchor (for example, a knotless SutureTak®) simplifies arthroscopic repair by combining a proven and reproducible suture anchor insertion procedure with knotless soft tissue fixation. FIGS. 9-11 show flexible strand 30, preferably a UHMWPE suture, preloaded onto the anchor 10 by tying static knot 31, which prevents flexible strand 30 from passing through distal blind hole 12 a. Flexible strand 30 is pre-attached to suture passing device 40 (for example, a FiberLink® or a Nitinol loop 40) which is threaded through flexible strand 30 (as shown by splice region 39 in FIG. 9). As explained above, flexible strand 30 is pre-loaded on anchor 10, which is loaded onto a driver (not shown in FIGS. 9-11). Flexible strand 30 is tied to the driver (for example, wrapped around a cleft of the driver) to fasten tensionable knotless anchor 10 securely to the driver. Prior to securing knotless anchor 10 to the driver, the suture passing device 40 is attached (threaded through splice region 39) to the flexible strand 30. The construct is inserted into bone, the flexible strand 30 untied from the driver, and the driver removed.

FIG. 9 illustrates the use of a reverse-loop suture lasso in a method aimed at preventing loop enlargement. After anchor 10 is implanted into hard tissue/bone 80, flexible strand 30 remains outside of a cannula 92. A suture retrieval instrument, for example curved SutureLasso™ instrument 62, is inserted into the anteroinferior cannula 92 and passed through soft tissue 50 near anchor 10. A suture passing device 140, which can be similar to suture passing device 40, has a nitinol loop 144 outside the anterosuperior cannula 92 and a tensioning end 142 passing through a second cannula 94. Flexible strand 30 is passed through nitinol loop 144, and tensioning end 142 is pulled such that flexible strand 30 is pulled through the top of tissue 50. Suture passing device 140 is then discarded.

FIG. 10 illustrates flexible strand 30 then being passed through nitinol loop 44, and tensioning end 42 of suture passing device 40 is pulled to pass flexible strand 30 through itself, creating a tensionable finger-trap loop 35.

FIG. 11 illustrates the final repair 150. Pulling the portion flexible strand 30 that rests above tissue 50 will tighten sheath portion 36 over core portion 37, creating a construct that will not slip. After desired tension is achieved, any remaining portion of flexible strand 30 may be removed and discarded.

Figure 14:
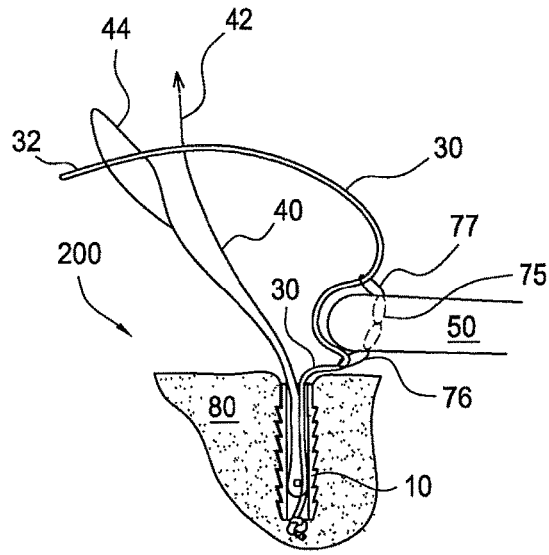
Figure 15:
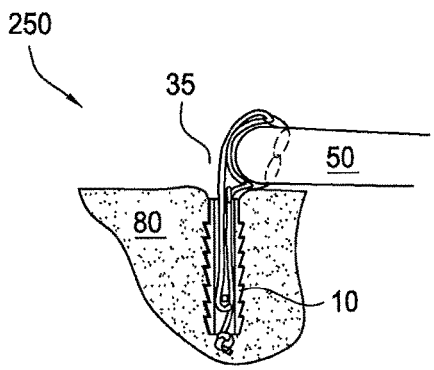

FIGS. 12-15 illustrate another exemplary method of anchoring surgical construct 200 of the present invention, which can comprise any of the tensionable anchors described herein to obtain repair 250 (FIG. 15). For example, the tensionable anchor can be tensionable anchor 10 assembled with flexible construct 199 formed of flexible strand or flexible material 30, shuttle/pull device 40 (suture passing instrument such as FiberLink® 40 or a nitinol loop 40) attached to the flexible strand 30, and suture chain 75 (FiberChain® 75). FiberChain® 75 can be loaded onto flexible strand 30 either before or after FiberChain® 75 is passed through tissue 50. For example, FiberChain® 75 may be passed through tissue 75, and then loaded onto flexible strand 30 by passing flexible strand 30 through an end loop 76 (terminating loop 76) of suture chain 75, for example, FiberChain® 75. Alternatively, flexible strand 30 may be passed through terminating loop 76 of FiberChain® 75, and then FiberChain® 75 is passed through tissue 50.

After FiberChain® 75 is passed through tissue 50 and loaded onto flexible strand 30, FiberChain® 75 is pulled up through cannula 92, and acts as a leader to pull flexible strand 30 up through cannula 92. Outside cannula 92, flexible strand 30 is passed through a second loop 77 of FiberChain® 75. End 32 of flexible strand 30 is then tensioned to center the two loops/links of FiberChain® 75 in tissue 50. The remainder of FiberChain® 75 is then removed, leaving two FiberChain® loops 76, 77 passing through tissue 50, where flexible strand 30 passes through each FiberChain® loop 76, 77 but does not pass through tissue 50, as illustrated in FIG. 14.

FIG. 14 further illustrates flexible strand 30 passing through nitinol loop 44 of suture passing device 40, and tensioning end 42 of suture passing device 40 is pulled to splice flexible strand 30 through itself, creating tensionable loop 35 that is point-loaded by FiberChain® 75. After desired tension is achieved, any remaining portion of flexible strand 30 may be removed and discarded. FIG. 15 illustrates final repair 250.

Figure 18:
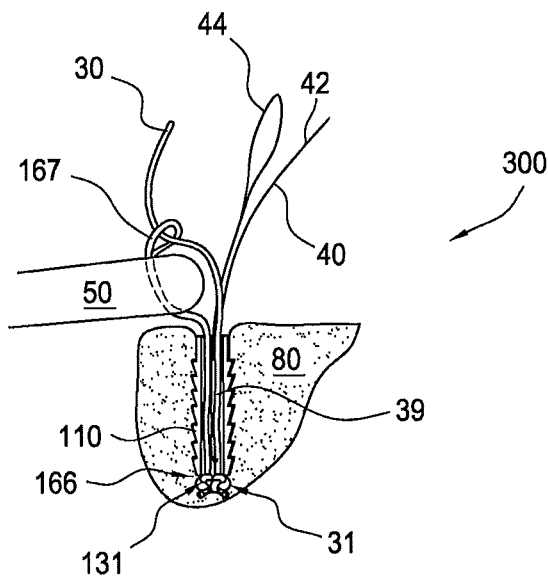
Figure 19:
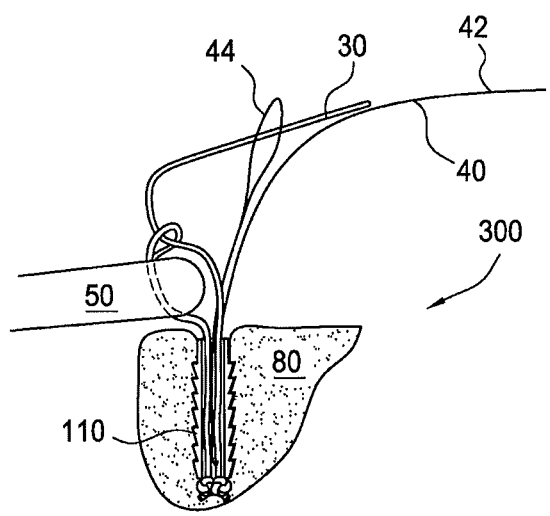
Figure 20:
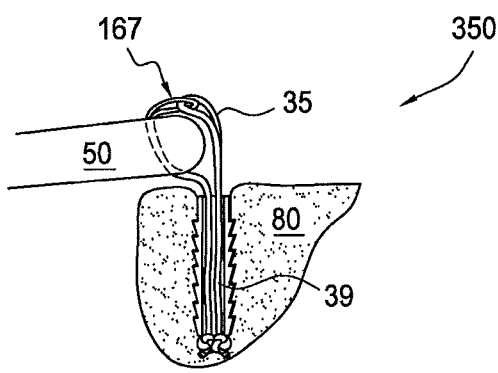
Figure 21:
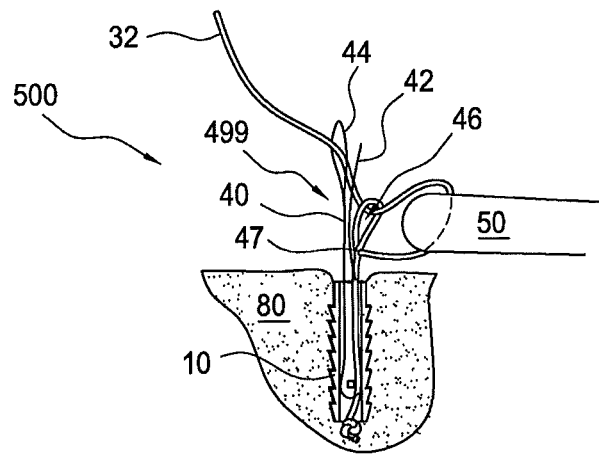
FIGS. 21-24 illustrate subsequent steps of a method of knotless repair according to an exemplary embodiment of the present invention.

FIGS. 16-20 illustrate another exemplary method of anchoring surgical construct 300 of the present invention using anchor 110 as described in FIGS. 4 and 5, to obtain tissue repair 350 (FIG. 20). Alternatively, surgical construct 400 and anchor 210 may be used for this method.

Figure 16:
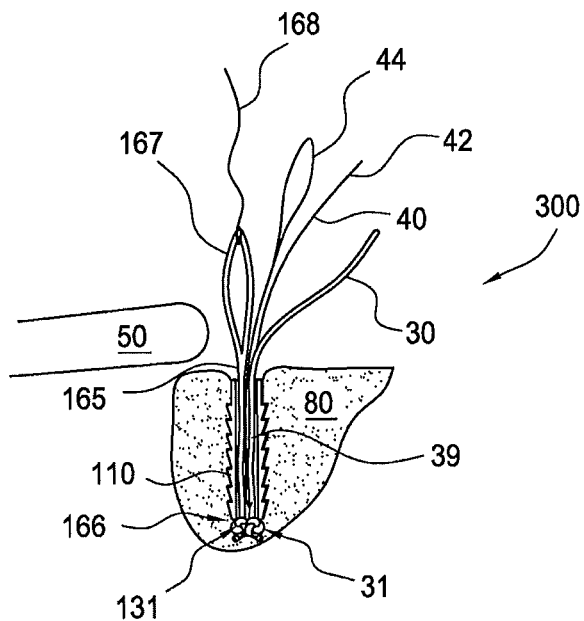
FIGS. 16-20 illustrate subsequent steps of a method of knotless repair according to an exemplary embodiment of the present invention.

FIG. 16 shows flexible strand 30, preferably a UHMWPE suture, preloaded onto the anchor 110 by tying static knot 31, which prevents flexible strand 30 from passing through distal blind hole 112 a. Flexible strand 30 is pre-attached to suture passing device 40 (for example, a FiberLink® or a Nitinol loop 40) which is threaded through flexible strand 30 (as shown by splice region 39 in FIG. 16). As explained above, flexible strand 30 is pre-loaded on anchor 110, which is loaded onto a driver (not shown in FIGS. 16-20). Flexible strand 30 is tied to the driver (for example, wrapped around a cleft of the driver) to fasten tensionable knotless anchor 110 securely to the driver. Prior to securing knotless anchor 110 to the driver, fixed loop construct 165 can be preloaded onto anchor 110 by tying static knot 131, which prevents fixed loop construct 165 from passing through distal blind hole 112a. The fixed loop construct 165 may also be preloaded by insert molding or by any other means known in the art. The construct is inserted into bone, the flexible strand 30 untied from the driver, and the driver removed.

Figure 17:
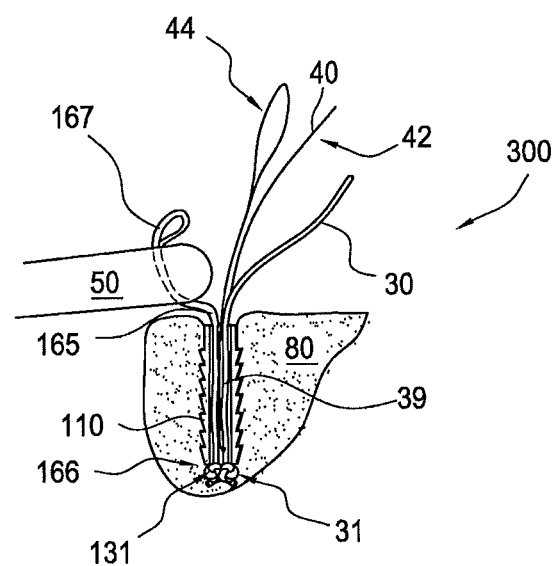

FIG. 17 illustrates fixed loop 167 of fixed loop construct 165 passed through tissue 50 (for example, labrum tissue), either with or without the aid of passing suture 168. Flexible strand 30 is then passed through fixed loop 167, as shown in FIG. 18.

FIG. 19 illustrates flexible strand 30 being passed through nitinol loop 44, and then tensioning end 42 of suture passing device 40 is pulled so that flexible strand 30 is passed through itself inside tensionable knotless anchor 110. FIG. 20 illustrates final repair 350 with flexible strand 30 after it has been pulled through itself, creating a splice at splice region 39 and tensionable loop 35. The suture passing device 40 (not visible anymore in FIG. 20 as it has been completely pulled out of the flexible strand 30) helps create splice 33 within tensionable knotless anchor 110 by facilitating flexible strand 30 passing through itself. The final repair shows tensionable loop 35 point-loaded by fixed loop 167 at or near its apex to create a repair that will not slip. After desired tension is achieved, any remaining portion of flexible strand 30 may be removed and discarded. As previously indicated, surgical construct 400 and anchor 210 may be used interchangeably with surgical construct 300 and anchor 110.

Figure 22:
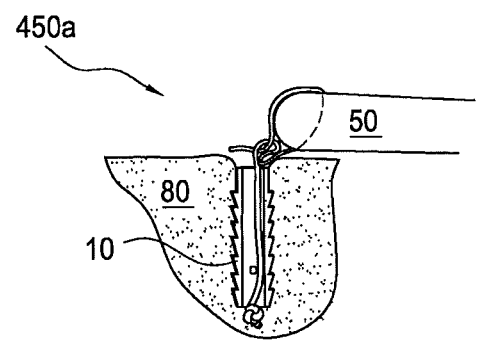
Figure 23:
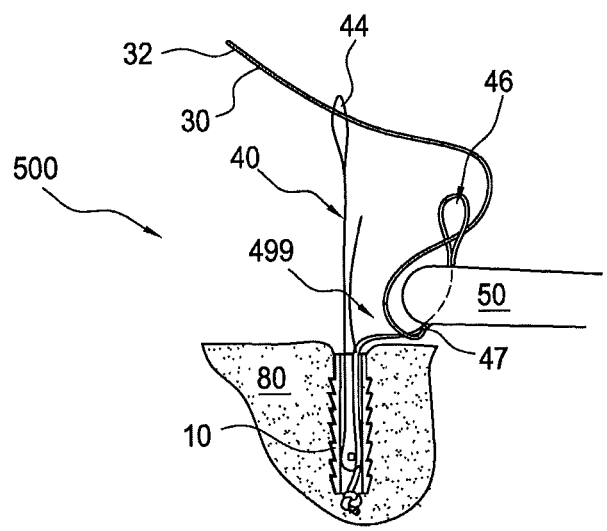
Figure 24:
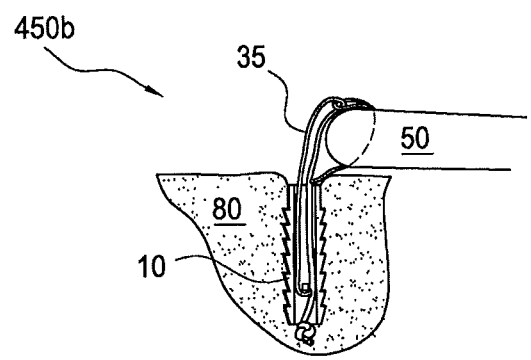

FIGS. 21-24 illustrate two different intersecting slip-loop knotless anchor methods of the present invention using flexible construct 499 and surgical construct 500 to obtain tissue repair 450a (FIG. 22) and 450b (FIG. 24). Option A (FIGS. 21-22) includes flexible strand 30 and suture passing device 40 as previously described. Flexible strand 30 is loaded into a needle and threaded through itself at an intersection point 47 to create slip loop 46. Intersection point 47 can be located near anchor 10.

After creating loop 46, flexible strand 30 is passed through tissue 50 and then through nitinol loop 44 of suture passing device 40. Tensioning end 42 of suture passing device 40 is then pulled in order to pull flexible strand 30 through itself to create splice 33 and tensionable loop 35. FIG. 22 shows final repair 450a after suture passing device 40 has been pulled through and discarded, and any remainder of tensioning strand 30 has been discarded.

FIGS. 23 and 24 illustrate Option B for an intersecting slip-loop knotless anchor. Option B is similar to Option A except that instead of passing flexible strand 30 through tissue 50, loop 46 is passed through tissue 50. Flexible strand 30 is then passed through loop 46 and nitinol loop 44 of suture passing device 40. Tensioning end 42 of suture passing device 40 is then pulled in order to pull flexible strand 30 through itself to create splice 33 and tensionable loop 35. FIG. 24 shows final repair 450b after suture passing device 40 has been pulled through and discarded. Tensionable loop 35 is point-loaded by loop 46 in order to create a repair that does not slip.

Figure 26:
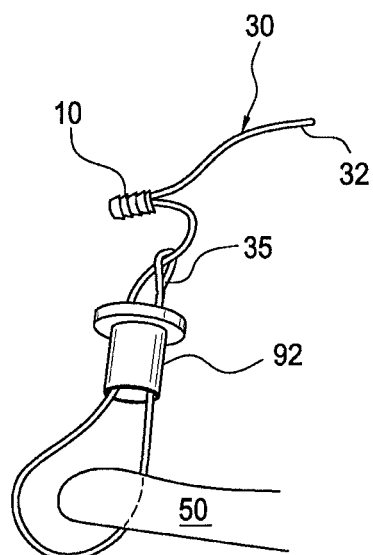
Figure 27:
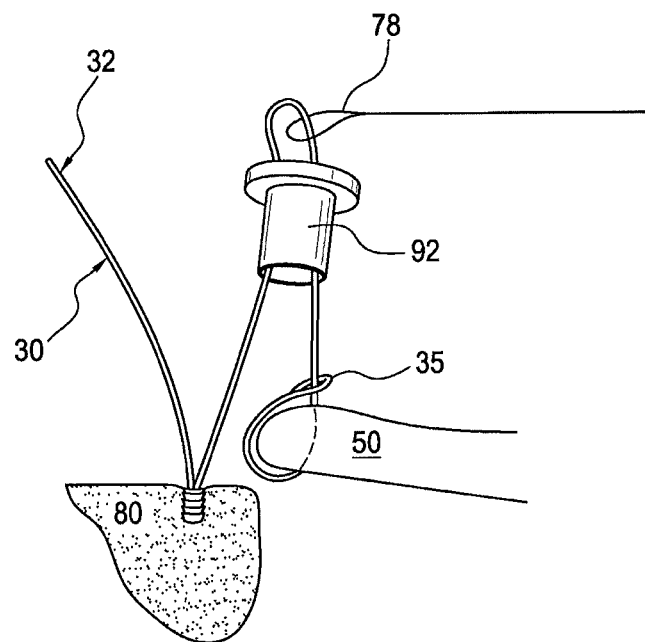
Figure 28:
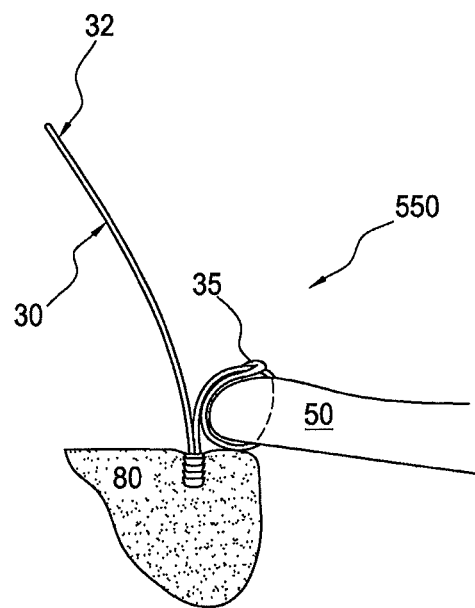

FIGS. 25-28 illustrate an exemplary embodiment according to present invention which includes any tensionable anchor previously described to achieve tissue repair 550 (FIG. 28). For example, the tensionable anchor can be tensionable anchor 10 assembled with a pre-threaded flexible strand 30 having a tensionable loop 35. In this embodiment, suture passing device 40 is not needed as the tensionable loop is already pre-configured.

Figure 25:
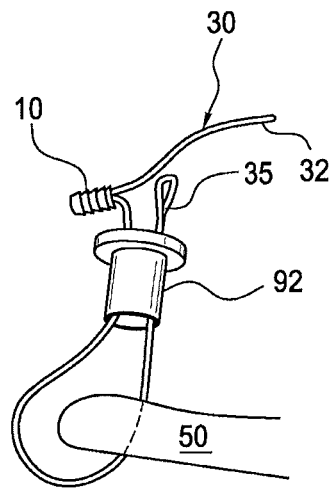
FIGS. 25-28 illustrate subsequent steps of a method of knotless repair according to an exemplary embodiment of the present invention.

FIG. 25 illustrates step 1, which includes passing tensionable loop 35 through tissue 50 (for example, the labrum) before anchor 10 has been implanted. Loop 35 may be passed through the top or the bottom of tissue 50, but is illustrated as being passed from bottom to top and then pulled out through portal 92.

FIG. 26 shows anchor 10 then being passed through loop 35, and then secured to a modified inserter (not shown), wherein the inserter is modified to have an open section to accommodate sutures exiting the side of the inserter tip. Anchor 10 is then implanted into hard tissue 80, as shown in FIG. 27. A traction loop 78 may optionally be used to keep tension on loop 35 as flexible strand end 32 is pulled.

FIG. 28 illustrates final repair 550 after flexible strand end 32 is pulled to reduce soft tissue 50 down to hard tissue 80. Final construct 550 shows loop 35 point-loaded by itself to create a repair that will not slip. After desired tension is achieved, any remaining portion of flexible strand 30 may be removed and discarded.

Figure 29:
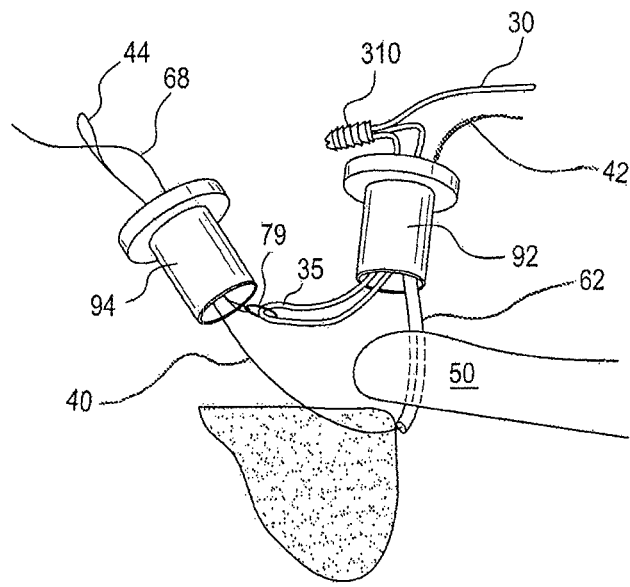
FIGS. 29-33 illustrate subsequent steps of a method of knotless repair according to an exemplary embodiment of the present invention.
Figure 30:
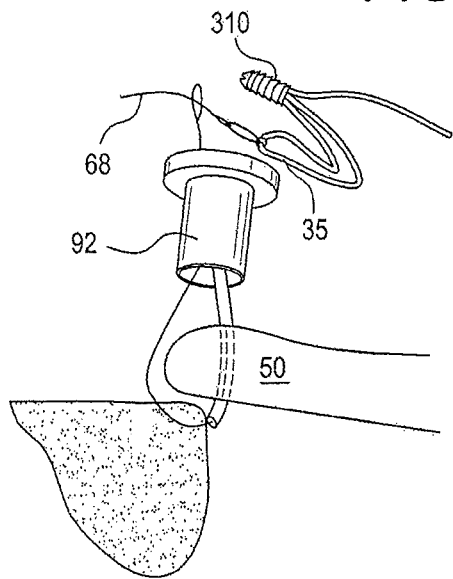
Figure 31:
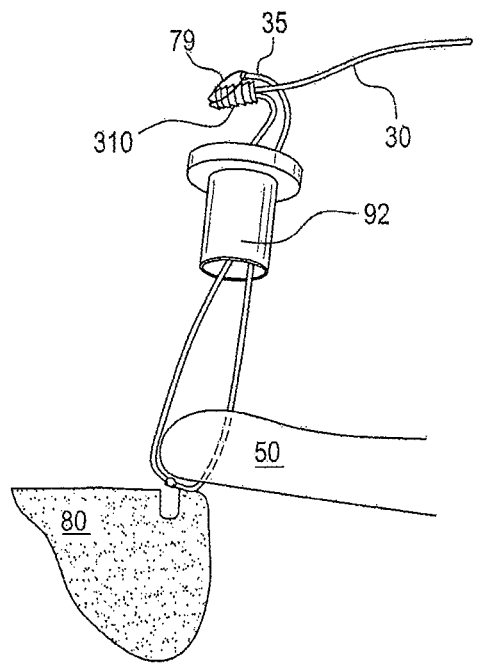
Figure 32:
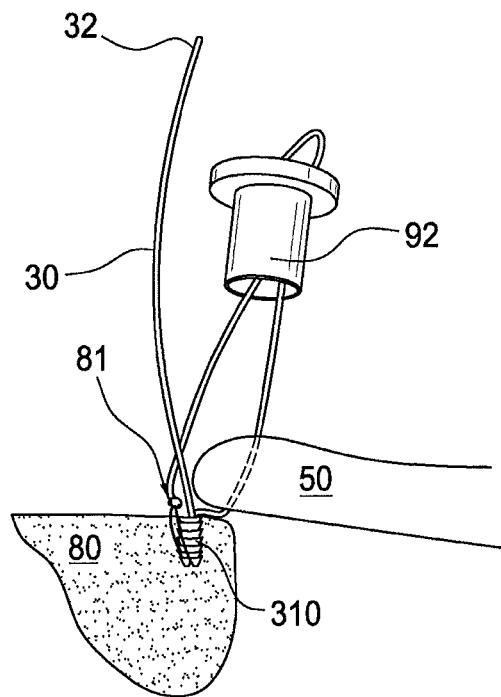
Figure 33:
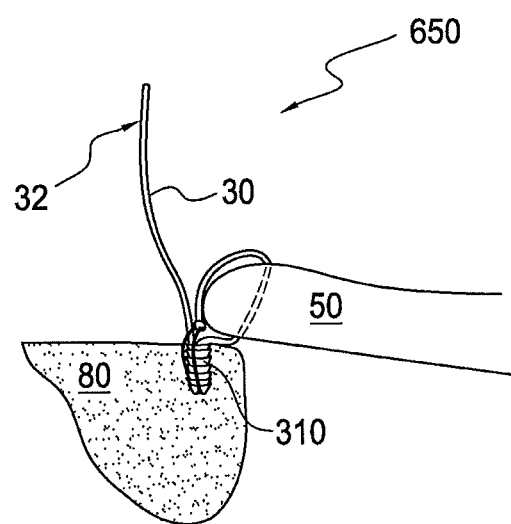

FIGS. 29-33 illustrate an exemplary method of tissue repair using knotless anchor 310 to achieve tissue repair 650 (FIG. 33). FIG. 29 illustrates anchor 310 with pre-threaded flexible strand 30, wherein flexible strand 30 has tensionable loop 35 pre-configured. An additional small fixed-length loop 79 is threaded through loop 35. Suture lasso instrument 62 is passed through cannula 92 and then through tissue 50. Suture passing device 40 passes through suture lasso instrument 62, wherein tensioning end 42 of suture passing device 40 passes through cannula 92 and nitinol loop 44 passes through a second cannula 94. Anchor 310 is disposed outside of the cannula 92, and tensionable loop 35 and fixed-length loop 79 are passed down through cannula 92 and then up through second cannula 94. Fixed-length loop 79 and flexible strand 30 are then passed through nitinol loop 44. FIG. 30 illustrates an alternative to FIG. 29 using one cannula 92 instead of two cannulas 92 and 94. Passing suture 68 may optionally be used to aid in passing fixed-length loop 79.

FIG. 31 illustrates nitinol loop 44 being pulled up through cannula 92, which pulls loop 35 and fixed-length loop 79 around the outside of tissue 50 and then up through tissue 50. Outside of cannula 92, fixed-length loop 79 is hooked onto slot 326 of anchor 310 and optional passing suture 68 discarded (if used).

FIG. 32 illustrates anchor 310 implanted into hard tissue 80. Slack is pulled out of loop 35 by pulling free end 32 of flexible strand 30. Small fixed-length loop 79 and tensionable loop 35 are joined at junction 81. FIG. 33 illustrates final repair 650 after end 32 has been tensioned to reduce soft tissue 50 down to hard tissue 80. After desired tension is achieved, any remaining portion of flexible strand 30 may be removed and discarded.

Figure 35:
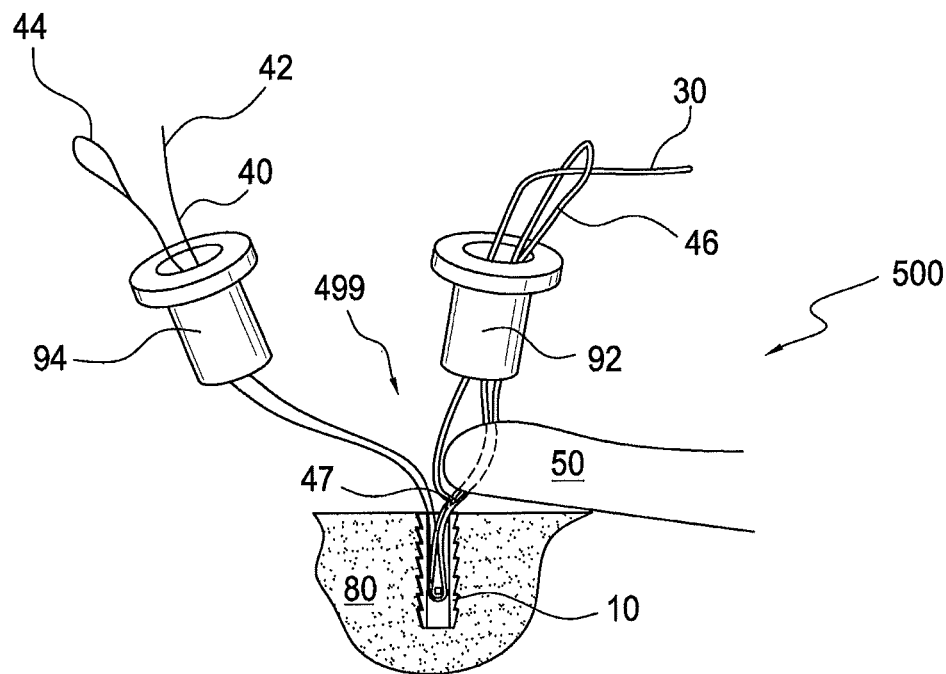
Figure 36:
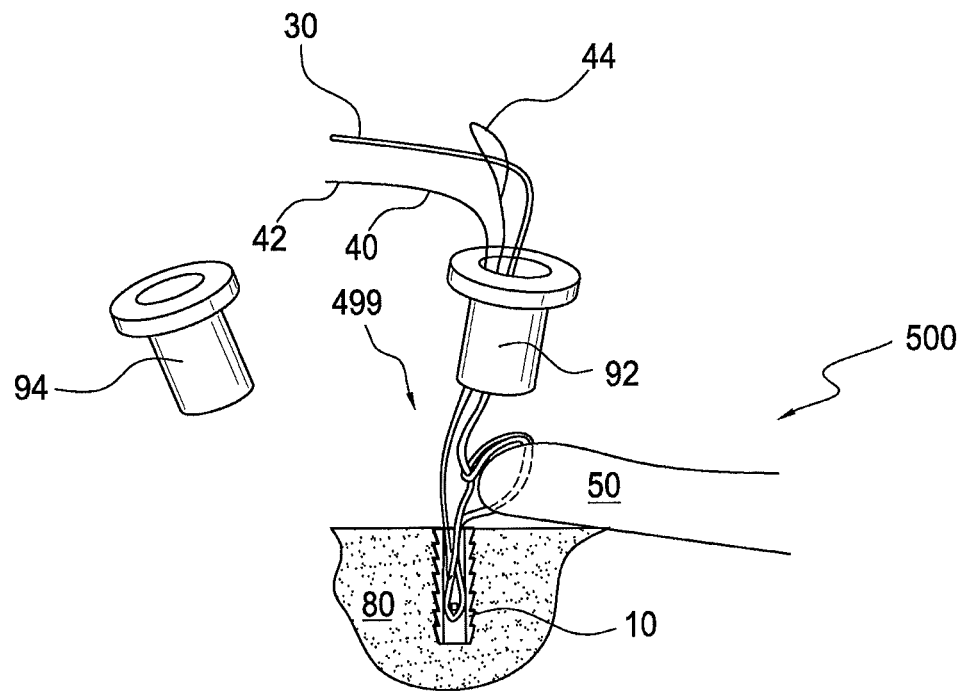
Figure 37:
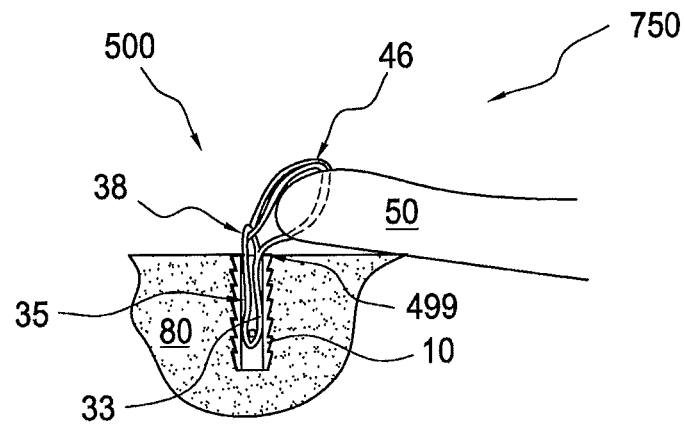
Figure 38:
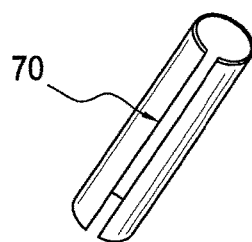
FIGS. 38-42 illustrate subsequent steps of another exemplary method of knotless repair according to a method of the present invention.
Figure 39:
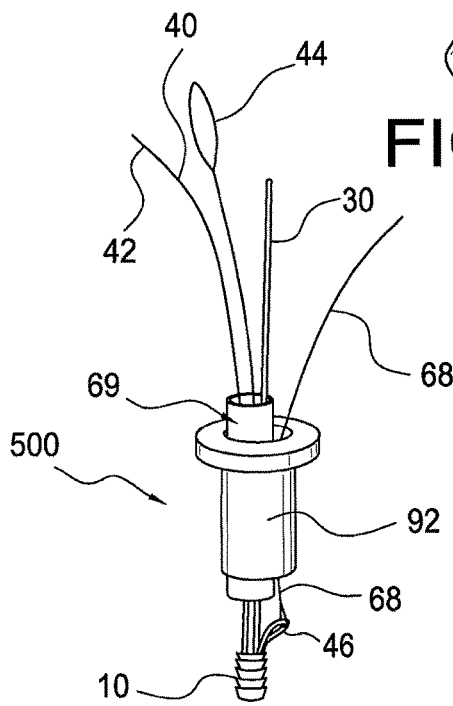

FIGS. 34-37 illustrate another exemplary embodiment of an intersecting slip-loop knotless anchor method of the present invention using surgical construct 500 having flexible construct 499 and knotless anchor 10 to obtain tissue repair 750 (FIG. 37).

Figure 34:
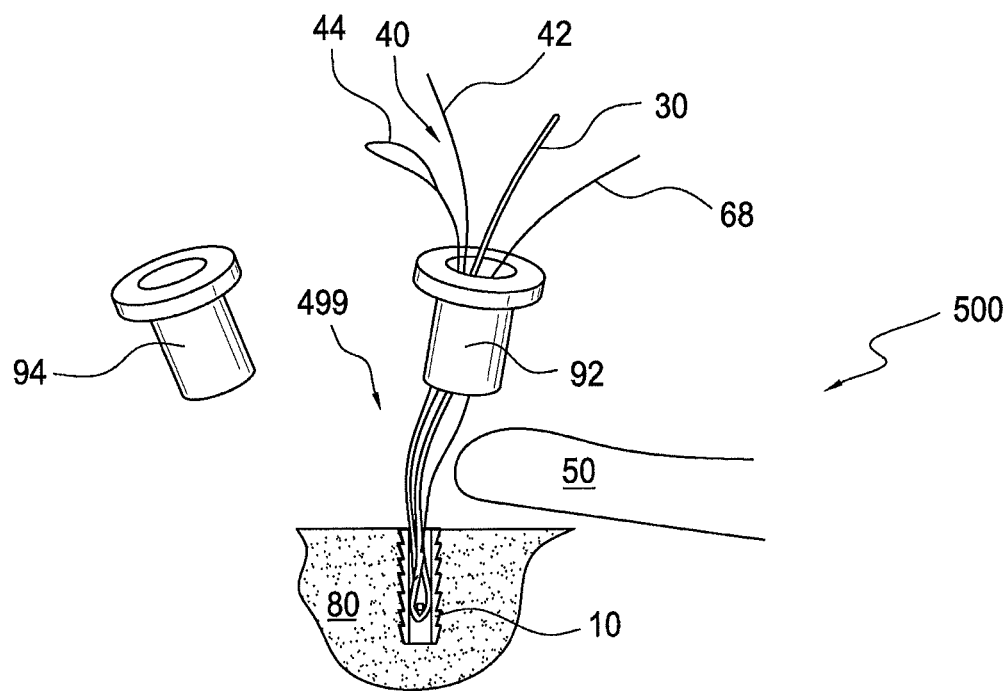
FIGS. 34-37 illustrate subsequent steps of a method of knotless repair according to an exemplary embodiment of the present invention.

FIG. 34 illustrates anchor 10 implanted into hard tissue 80. Anchor 10 includes flexible strand 30 and suture passing device 40 as previously described. Flexible strand 30 is loaded into a needle and threaded through itself at an intersection point 47 to create a slip-loop 46. An optional passing suture 68 may be used to aid in passing slip-loop 46 through soft tissue 50. Intersection point 47 can be located near anchor 10. Alternatively, flexible strand 30 may be pre-configured with slip-loop 46 and intersection point 47 to simplify the procedure during operation.

Slip-loop 46 is passed up through soft tissue 50, and passing suture (if used) is discarded. At this point, slip-loop 46 and flexible strand 30 are outside of cannula 92. Flexible strand 30 is then passed through slip-loop 46, and suture passing device 40 (including nitinol loop 44 and tensioning end 42) are retrieved up through second cannula 94 to prevent tangling, as illustrated in FIG. 35.

FIG. 36 shows flexible strand 30 tensioned to reduce slip-loop 46 down over soft tissue 50. Suture passing device 40 (including nitinol loop 44 and tensioning end 42) is removed from second cannula 94 and passed up through first cannula 92. Flexible strand 30 is then passed through nitinol loop 44, and tensioning end 42 of suture passing device 40 is then pulled to pull flexible strand 30 through itself to create splice 33 and tensionable loop 35. After desired tension is achieved, any remaining portion of flexible strand 30 may be removed and discarded. FIG. 37 shows final repair 750 where tensionable loop 35 is point-loaded by slip-loop 46 at or near its apex 38 to create a repair that will not slip.

Figure 40:
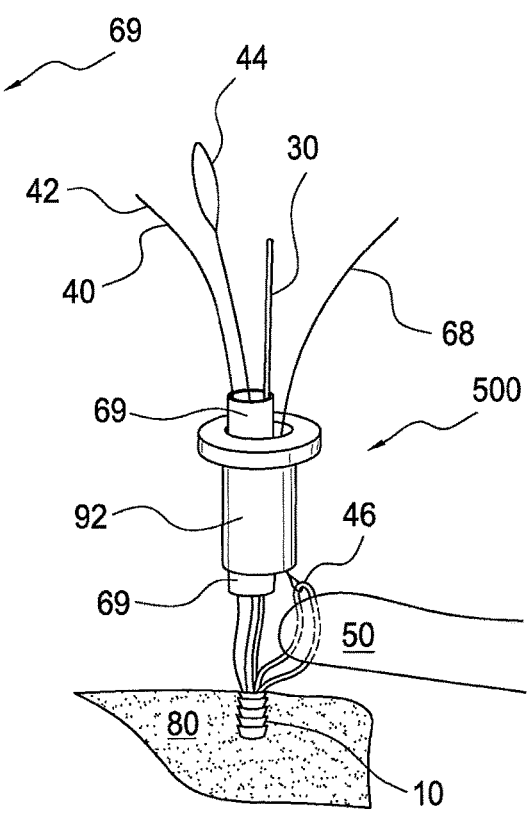
Figure 41:
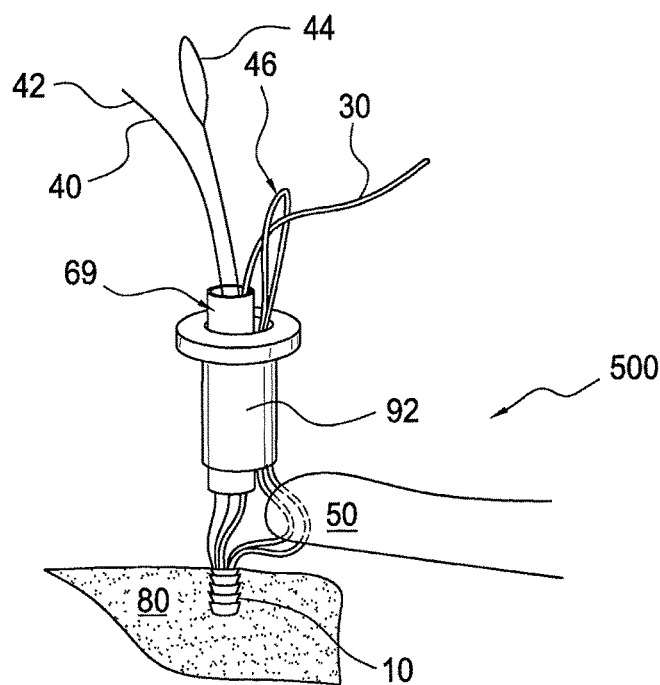
Figure 42:
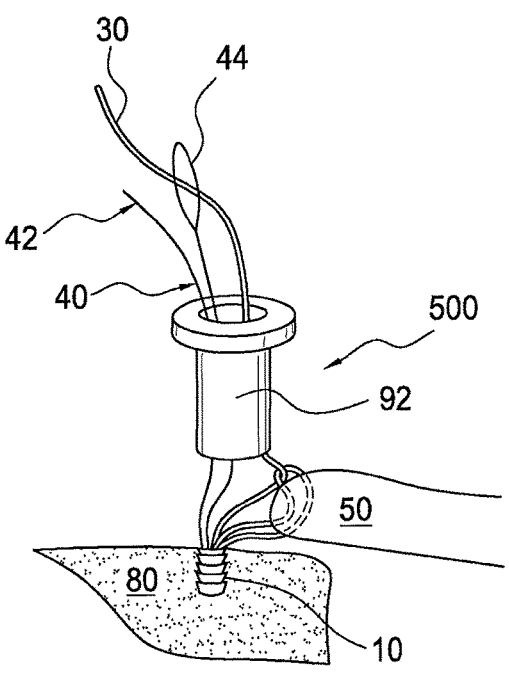

FIGS. 38-42 illustrate another embodiment of a slip-loop knotless anchor method of the present invention using surgical construct 500 having flexible construct 499 and knotless anchor 10, and utilizing only a first cannula 92 to achieve repair 850 (FIG. 42). Cannula 92 is configured to have a semi-rigid tube 69 with a slit 70 extending the entire length of tube 69. Suture passing device 40 (nitinol wire 40 and nitinol loop 44) and flexible strand 30 pass through tube 69. Flexible strand 30 can have slip-loop 46 pre-made prior to being affixed to anchor 10. Passing suture 68 can wrap around slip-loop 46 to aid in passing loop 46 through soft tissue 50.

FIG. 40 illustrates passing suture 68 being passed through tissue 50 and pulled through such that loop 46 is pulled through tissue 50 and up through cannula 92.

FIG. 41 illustrates flexible strand 30 being pulled out from tube 69 and passed through loop 46. Flexible strand 30 is then tensioned to cinch down slip-loop 46.

FIG. 42 illustrates flexible strand 30 passing through nitinol loop 44, and tensioning end 42 of suture passing device 40 is then pulled to pull flexible strand 30 through itself, creating tensionable loop 35 that is point-loaded by slip-loop 46. After desired tension is achieved, any remaining portion of flexible strand 30 may be removed and discarded to obtain tissue repair 850.

The surgical suture knotless constructs and systems described above confer a point-loading mechanism which eliminates the need for loading suture outside the tensionable knotless construct (anchor). The construct may include a tensionable loop that can be point-loaded by additional fixed loops or suture chains. An exemplary surgical system for tissue repairs of the present invention comprises a fixation device comprising a cannulated body, a longitudinal axis, a proximal end, and a distal end; a fixed loop construct secured to the fixation device, the fixed loop construct comprising a first flexible strand having a fixed loop and a distal end, wherein the fixed loop construct is secured to the fixation device at the distal end; and a flexible construct comprising a second flexible strand and a shuttling device provided within the second flexible strand, wherein both the second flexible strand and the shuttling device extend through the cannulated body of the fixation device and along the longitudinal axis. The shuttling device is pulled out of the body of the fixation device such that the second flexible strand first passes through the fixed loop of the fixed loop construct and then through an eyelet of the shuttling device and through itself to form a knotless closed loop with an adjustable perimeter and a splice that is point-loaded by the fixed loop construct.

An exemplary method of tissue repair of the present invention may comprise the steps of: installing a fixation device in bone, the fixation device comprising a body, a flexible strand extending through at least a portion of the body and extending out of a first cannula, and a first shuttling device passing through a splice region of the flexible strand; passing a suture retrieval instrument through a soft tissue and retrieving a loop of a second shuttling device, the second shuttling device having a tensioning end passing through a second cannula; pulling the loop of the second shuttling device through the first cannula; passing the flexible strand through the loop of the second shuttling device; pulling the tensioning end of the second shuttling device to pull the flexible strand through a top side of the soft tissue; passing the flexible strand through a loop of the first shuttling device; and pulling a tensioning end of the first shuttling device to pull the flexible strand through the splice region of the flexible strand, thereby forming a knotless closed loop having an adjustable perimeter. The splice region may be located within or outside the body of the fixation device. The flexible strand may extend through the body of the fixation device.

The knotless suture constructs and systems of the present invention are used in conjunction with any knotless fixation devices which can allow a flexible strand and attached suture passing device to form a splice within the body of the fixation device. The fixation devices may be any of swivel and/or screw-in suture anchors and/or push-in suture anchors (such as an Arthrex SwiveLock® anchor, disclosed in U.S. Pat. No. 9,005,246, issued Apr. 14, 2015, or a PushLock® anchor, as disclosed in U.S. Pat. No. 7,329,272, issued Feb. 12, 2008, the entire disclosures of which are incorporated herein by reference). The fixation devices may also be any anchors, implants or screws (such as interference screws or tenodesis screws) or any fixation element that allows attachment/fixation of the knotless suture construct to bone. The fixation devices/implants may have various sizes (various diameters and/or lengths) and may be formed of biocompatible materials such as PEEK, biocomposite materials, metals and/or metal alloys, or combination of such materials, among others. The fixation devices may be unitary or may be multiple-piece constructs.

Surgical constructs and methods of forming flexible construct 499 can be any of those disclosed in U.S. Pat. No. 9,107,653, issued Aug. 18, 2015, the entire disclosure of which is incorporated herein by reference.

The flexible strand 30 may be a high-strength suture, such as an ultrahigh molecular weight polyethylene (UHMWPE) suture, which is the preferred material as this material allows easy splicing. Alternatively, the high strength suture may be a FiberWire® suture, which is disclosed and claimed in U.S. Pat. No. 6,716,234, issued Apr. 6, 2004, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM) fibers, braided with at least one other fiber, natural or synthetic, to form lengths of suture material.

The strands may also be formed of a stiff material, or combination of stiff and flexible materials, depending on the intended application. The strands may be also coated and/or provided in different colors. The knotless anchors of the present invention can be used with any type of flexible material or suture that forms a splice and a loop.

Although the terms "chain," "suture chain" and Fiber-Chain® have been used interchangeably in this application, it must be understood that the term "chain" is not limited to only "suture chain" or FiberChain®; rather, the term "chain" encompasses a plurality of loops of any material and of any dimension (i.e., loops of similar or different diameters), as long as the loops are interconnected to each other. An exemplary suture chain that may be used in the present application is described in U.S. Pat. No. 7,981,140, issued Jun. 14, 2007, the disclosure of which is incorporated by reference in its entirety herewith.

The knotless suture constructs also include sutures that are spliced—at least in part—in a manner similar to an Arthrex ACL TightRope®, such as disclosed in U.S. Pat. No. 8,439,976, issued May 14, 2013, and U.S. Pat. No. 8,460,379, issued Jun. 11, 2013, the entire disclosures of which are incorporated by reference in their entirety herein.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is to be limited not by the specific disclosure herein, but only by the appended claims.

What is claimed is:

1. A method for tissue repairs using a surgical fixation construct comprising a cannulated fixation device having a proximal end, a distal end, and a longitudinal axis extending through the proximal and distal ends, a flexible construct positioned at least partially in the fixation device, the flexible construct comprising a flexible strand having a free end and defining two apertures at different locations along a length of the flexible strand and a passage extending through the flexible strand and connecting the two apertures, and a shuttling device positioned at least partially in the fixation device, the method comprising:
- implanting the fixation device in bone;
- forming a first loop that passes through soft tissue after the implanting of the fixation device in the bone, wherein the first loop has an adjustable perimeter and at least part of the first loop is formed by the flexible strand;
- passing the free end of the flexible strand through the shuttling device while the shuttling device extends through the passage of the flexible strand;
- pulling the shuttling device out of the passage to shuttle the free end of the flexible strand through the passage of the flexible strand to form a splice and a second loop with an adjustable perimeter adjacent the splice; and
- further pulling the free end of the flexible strand through the passage to reduce the respective perimeters of the first and second loops to draw the soft tissue towards the bone.

2. The method of claim 1, wherein when the second loop is formed, the second loop is a knotless self-locking closed loop with the adjustable perimeter.

3. The method of claim 1, wherein the second loop is connected to the first loop adjacent the soft tissue to form a point-loaded loop along the second loop.

4. The method of claim 3, wherein the second loop is directly connected to the first loop.

5. The method of claim 4, wherein the second loop extends through the first loop to directly connect to the first loop.

6. The method of claim 3, wherein the point-loaded loop is formed away from the splice at or near an apex of the second loop.

7. The method of claim 1, wherein the flexible construct further comprises a pre-formed loop, and wherein the forming of the first loop through the soft tissue comprises passing one of the free end of the flexible strand or the pre-formed loop through the soft tissue and then passing the free end of the flexible strand through the pre-formed loop.

8. The method of claim 7, wherein the pre-formed loop is formed separately from the flexible construct by a second flexible strand.

9. The method of claim 8, wherein the second flexible strand comprises a suture chain that comprises a plurality of loops.

10. The method of claim 7, wherein the second loop is formed to extend through the pre-formed loop.

11. The method of claim 7, wherein the second flexible strand comprises a single fixed loop.

12. The method of claim 7, wherein the pre-formed loop is integrally formed with the flexible construct.

13. The method of claim 12, wherein the pre-formed loop is formed by passing the free end of the flexible strand transversely through another portion of the flexible strand prior to forming the first loop through the soft tissue.

14. The method of claim 1, wherein the splice is configured to be formed at least partially within the fixation device.

15. The method of claim 1, wherein the fixation device is a suture anchor.

16. The method of claim 15, wherein the suture anchor comprises a post, and wherein the flexible construct extends around the post.

17. The method of claim 1, wherein at least part of the flexible construct comprises a slip loop formed by passing the free end of the flexible strand transversely through another portion of the flexible strand that is spaced apart from the passage of the flexible strand.

18. A method for tissue repairs using a surgical fixation construct comprising a cannulated fixation device having a proximal end, a distal end, and a longitudinal axis extending through the proximal and distal ends, a flexible construct positioned at least partially in the fixation device, the flexible construct comprising a flexible strand having a fixed end and a free end and defining two apertures at different locations along a length of the flexible strand and a passage extending through the flexible strand and connecting the two apertures, and a shuttling device positioned at least partially in the fixation device, the method comprising:
- implanting the fixation device in bone;
- forming part of a loop that passes through soft tissue after the implanting of the fixation device in the bone, wherein at least a portion of the loop is formed by a region of the flexible strand that extends from the fixed end away from the bone and around an outside of the soft tissue in a direction away from the fixed end;
- passing the free end of the flexible strand through the shuttling device while the shuttling device extends through the passage of the flexible strand;
- pulling the shuttling device out of the passage to shuttle the free end of the flexible strand through the passage of the flexible strand to form a splice; and
- further pulling the free end of the flexible strand through the passage to draw the soft tissue towards the bone.

19. The method of claim 18, wherein the loop that passes through the soft tissue is a first loop, and wherein a second loop that is connected to the first loop is formed adjacent the splice.

20. The method of claim 18, wherein the splice is formed along a perimeter of the loop.

* * * * *